US009550023B2

(12) United States Patent
Pang et al.

(10) Patent No.: US 9,550,023 B2
(45) Date of Patent: Jan. 24, 2017

(54) METHOD OF MAKING A CORRUGATED DEFLECTION DIAPHRAGM

(71) Applicants: Changlin Pang, Pasadena, CA (US); Jason Shih, Yorba Linda, CA (US); Fukang Jiang, Arcadia, CA (US); Changgeng Liu, South Pasadena, CA (US); Sean Caffey, Pasadena, CA (US); Andrew Urazaki, Arcadia, CA (US)

(72) Inventors: Changlin Pang, Pasadena, CA (US); Jason Shih, Yorba Linda, CA (US); Fukang Jiang, Arcadia, CA (US); Changgeng Liu, South Pasadena, CA (US); Sean Caffey, Pasadena, CA (US); Andrew Urazaki, Arcadia, CA (US)

(73) Assignee: MiniPumps, LLC, Pasadena, CA (US)

( * ) Notice: Subject to any disclaimer, the term of this patent is extended or adjusted under 35 U.S.C. 154(b) by 159 days.

(21) Appl. No.: 14/317,854

(22) Filed: Jun. 27, 2014

(65) Prior Publication Data
US 2015/0005709 A1 Jan. 1, 2015

Related U.S. Application Data

(60) Provisional application No. 61/840,150, filed on Jun. 27, 2013.

(51) Int. Cl.
B29C 59/14 (2006.01)
A61M 5/145 (2006.01)
(Continued)

(52) U.S. Cl.
CPC ..... A61M 5/14586 (2013.01); A61M 5/14276 (2013.01); B29C 59/14 (2013.01);
(Continued)

(58) Field of Classification Search
None
See application file for complete search history.

(56) References Cited

U.S. PATENT DOCUMENTS

| 2006/0225510 | A1* | 10/2006 | Wong | A61B 5/0084 73/705 |
| 2007/0012891 | A1 | 1/2007 | Maltezos et al. | |
| 2009/0047797 | A1* | 2/2009 | Anderson | H01L 23/3135 438/763 |
| 2009/0306594 | A1* | 12/2009 | Pang | A61F 9/00781 604/133 |
| 2014/0332997 | A1* | 11/2014 | Shih | B29C 41/42 264/138 |
| 2015/0125952 | A1* | 5/2015 | Kim | A61L 27/14 435/366 |

FOREIGN PATENT DOCUMENTS

| WO | 00/29770 A2 | 5/2000 |
| WO | 01/22776 A1 | 3/2001 |
| WO | 2007/106557 A2 | 9/2007 |

OTHER PUBLICATIONS

Luharuka et al., "Improved Manufacturability and Characterization of a Corrugated Parylene Diaphragm Pressure Transducer", Journal of Micromechanics and Microengineering, vol. 16, No. 8, Aug. 1, 2006, pp. 1468-1474.

(Continued)

Primary Examiner — Shamim Ahmed
(74) Attorney, Agent, or Firm — Morgan, Lewis & Bockius LLP

(57) ABSTRACT

A removable material is deposited or otherwise applied to a flat substrate surface in a pattern corresponding to desired corrugations in a membrane, e.g., a deflection diaphragm. The applied material serves as a scaffold for a polymeric material, which is applied thereover, and following cure or hardening, the polymeric material is removed to form a finished corrugated membrane.

17 Claims, 1 Drawing Sheet

(51) Int. Cl.
*B44C 1/22* (2006.01)
*F04B 43/00* (2006.01)
*F04B 45/04* (2006.01)
*B81C 99/00* (2010.01)
*A61M 5/142* (2006.01)
*B29K 23/00* (2006.01)
*F16K 99/00* (2006.01)

(52) U.S. Cl.
CPC ........ *B81C 99/008* (2013.01); *F04B 43/0054* (2013.01); *F04B 45/04* (2013.01); *A61M 2005/14204* (2013.01); *B29C 2791/004* (2013.01); *B29K 2023/00* (2013.01); *B81B 2203/0127* (2013.01); *B81C 2201/0108* (2013.01); *F16K 2099/008* (2013.01)

(56) References Cited

OTHER PUBLICATIONS

PCT International Patent Application No. PCT/US2014/044621, International Search Report and Written Opinion mailed Oct. 23, 2014, 16 pages.

Sim et al., "Theoretical and Experimental Studies on the Parylene Diaphragms for Microdevices", Microsystem Technologies, vol. 11, No. 1, Jan. 1, 2005, pp. 11-15.

* cited by examiner

METHOD OF MAKING A CORRUGATED DEFLECTION DIAPHRAGM

CROSS-REFERENCE TO RELATED APPLICATIONS

The present application claims priority to, and the benefits of, U.S. Ser. No. 61/840,150, filed on Jun. 27, 2013, the entire disclosure of which is hereby incorporated by reference.

FIELD OF THE INVENTION

In various embodiments, the present invention relates generally to manufacture of pump devices and, more specifically, to fabrication of corrugated membranes for electrolytic pumps.

BACKGROUND

As patients live longer and are diagnosed with chronic and often debilitating ailments, the result will be an increase in the need to place protein therapeutics, small-molecule drugs and other medications into targeted areas throughout the body that are currently inaccessible or inconvenient as sites of administration. For example, many vision-threatening diseases, including retinitis pigmentosa, age-related macular degeneration (AMD), diabetic retinopathy, and glaucoma, are incurable and yet difficult to treat with currently available therapies: oral medications have systemic side effects; topical applications may sting and engender poor compliance; injections require a medical visit, can be painful and risk infection; and sustained-release implants must typically be removed after their supply is exhausted (and offer limited ability to change the dose in response to the clinical picture). Another example is cancer, such as breast cancer or meningiomas, where large doses of highly toxic chemotherapies such as rapamycin or irinotecan (CPT-11) are administered to the patient intravenously, resulting in numerous undesired side effects outside the targeted area. Various other target sites (e.g., the eye, brain, ear, kidney, pancreas, etc.) may be accessed with specifically tailored drug pumps fluidically connected to site-appropriate catheters or diffusion membranes.

Implantable drug-delivery systems, which may include a refillable drug reservoir, an actuation mechanism, a cannula and check valve, etc., allow for controlled delivery of pharmaceutical solutions to a specified target. This approach can minimize the surgical incision needed for implantation and avoids future or repeated invasive surgery or procedures. These implantable drug-delivery devices may be fabricated using parylene (a widely-used polymer of p-xylene) and/or other biocompatible material to achieve an active device with full biocompatibility. The pump may be used for delivery of, for example, fluid, cells, biologics, or a suspension of inorganic and/or organic particles into the body of human or animal subjects.

Implantable drug delivery systems may be actuated in many different ways. For example, an electrolytic pump offers several advantages for drug-delivery applications. Their low-temperature, low-voltage and low-power operation makes them well-suited for long-term operation in vivo. Additionally, the gas evolution proceeds even in a pressurized environment (e.g., 200 MPa) and produces oxygen and hydrogen gases that contribute to a volume expansion of about a thousand times greater than that of the electrolyte (e.g., water) used in the reaction, creating an actuation force with a minimal physical footprint. The invention may also be implemented in non-implantable drug-delivery systems such as patch pumps.

A key component of many electrolytic drug-delivery pumps is a force-transducing medium (flexible membrane, piston, deflection diaphragm), which separates the electrolysis chamber and the drug reservoir. The diaphragm temporarily deflects towards the drug reservoir under pressure generated in the electrolysis chamber during drug delivery. Once electrolysis is stopped and gas generation ceases, the gas reconstitutes in the presence of a catalyst (e.g., platinum) and the deflection diaphragm returns to its original conformation. For space efficiency, a deflection diaphragm may be provided with corrugations that increase the diaphragm's expansion volume without increasing its footprint. See, e.g., U.S. Pat. Nos. 8,285,328 and 8,348,897, the entire disclosures of which are hereby incorporated by reference. The higher the aspect ratio of the corrugations (i.e., the taller they are), the greater will be the amount of deflection that the pump will be capable of mechanically.

Typical fabrication schemes for corrugated membranes utilize some form of molding. For example, a polymer formulation may be deposited onto a patterned substrate and cured, following which the finished membrane is removed. Particularly for small-scale corrugated membranes for implantable electrolytic pumps, the substrate may be silicon patterned by, for example, etching. Thus, a photoresist may be applied to a flat silicon wafer in the pattern of the desired corrugations (i.e., one or more concentric circles, ovals, rectangles, etc.); the wafer is then etched (e.g., by deep reactive ion etching, or DRIE) so that the wafer regions underlying the photoresist are unaffected, thereby producing the mold. Such processes may exhibit limitations in terms of height tolerance control and height uniformity, and etching processes are costly.

SUMMARY

Embodiments of the invention utilize a removable material deposited or otherwise applied to a flat substrate surface in the pattern of the desired membrane corrugations. (As used herein, the terms "apply," "applied" or "application" refer to any form of material placement on a surface in order to form a pattern having height, including pointwise deposition, photopatterning (e.g., photolithography), screen printing, stenciling, lamination, surface-wide coating (e.g., spin coating) followed by selective removal (e.g., using a laser), and any other suitable application technique). The applied material serves as a scaffold for the polymeric material, which is applied thereover, and following cure or hardening, the polymer material is removed to form a finished corrugated membrane. The applied support material, in other words, is used directly as a "positive" mold pattern rather than as a mask to facilitate etching of the underlying substrate surface. Indeed, the removable material may be conventional photoresist. As mold-preparation processes in accordance with the present invention require only material application, there is no need for a costly DRIE step, or for the subsequent steps of oxidation and wet etching required to complete a traditional "negative" mold. Processes in accordance herewith make design changes easier and reduce manufacturing time. Although the mold must be remade for each membrane whereas a traditional silicon mold may be reused, the overall cost advantages and the benefits of reproducibility generally favor the present approach over etched silicon molds.

Accordingly, in a first aspect, the invention pertains to a method of manufacturing a corrugated diaphragm suitable for use in a pump. In various embodiments, the method comprises the steps of applying a chemically removable layer onto a substrate (e.g., silicon), the removable layer having a relief pattern therein; coating a membrane-forming layer comprising a hardenable polymer onto the patterned removable layer in a liquid phase; and following hardening of the hardenable polymer, removing the removable layer to release the membrane-forming layer, thereby forming the corrugated diaphragm with corrugations corresponding to the relief pattern.

The chemically removable layer may be applied as a uniform coating onto the substrate, and the method may further comprise the step of patterning the uniformly applied coating to obtain the relief pattern. The removable layer may be a photoresist and the patterning may comprise (a) patternwise exposing the photoresist to actinic radiation and (b) subjecting the exposed photoresist to a developer. For example, the photoresist may be a positive photoresist or a negative photoresist.

In some embodiments, the polymer is parylene. The method may further comprise the step of patterning the membrane-forming layer by oxygen plasma etching using a shadow mask following hardening of the membrane-forming layer. In some embodiments, the membrane-forming layer comprises or consists of a plurality of layers including at least one hardenable polymer layer and at least one metal layer.

The removing step may comprise subjecting the removable layer to a solvent therefor. In some embodiments, the method further comprises applying an additional release layer onto the substrate prior to applying the membrane-forming layer. The additional release layer may consist of a material different from the chemically removable layer. In these embodiments, the releasing step may comprise subjecting the additional release layer to a solvent therefor and subjecting the removable layer to a solvent therefor. The additional release layer may or may not consist of the same material as the chemically removable layer.

The chemically removable layer may be applied patternwise by deposition. The relief pattern may comprises or consist of concentric circles or concentric ovals.

In another aspect, the invention pertains to a device for administering a liquid. In various embodiments, the device comprises a housing; and within the housing, a pump assembly including a reservoir, an electrolytic forcing mechanism including an electrolysis reservoir and a force-transducing medium, and a cannula for conducting liquid from the reservoir to an ejection site exterior to the housing in response to pressure applied by the forcing mechanism. The force-transducing medium comprises or consists essentially of a recombination catalyst facing and in fluidic contact with an interior of the electrolysis reservoir. For example, the force-transducing medium may be a piston, deflection diaphragm or flexible membrane. The recombination catalyst may comprise or consist essentially of platinum.

The term "substantially" or "approximately" means±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Embodiments of the present invention utilize a pattern of a removable (e.g., chemically removable) material as a mold scaffold for fabrication of a corrugated deflection diaphragm. The diaphragm may be provided with different corrugation depths and lengths to accommodate the deflection requirements of a given electrolytic chamber.

Figure 1:
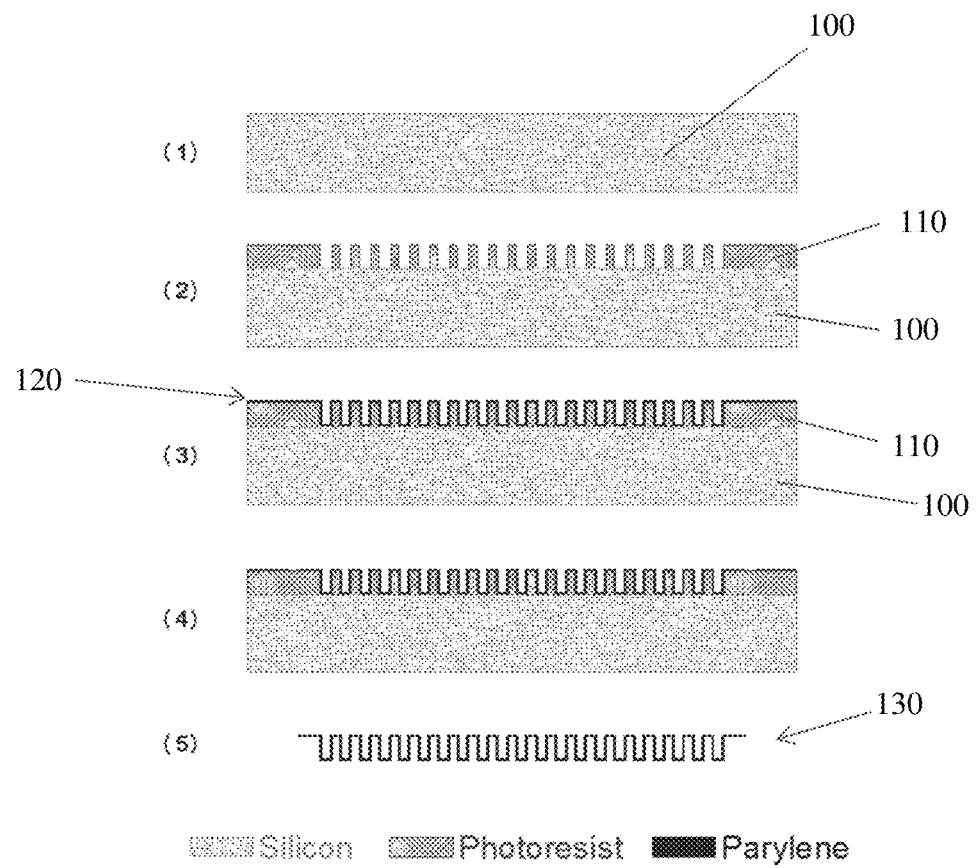
FIG. 1 schematically illustrates a representative embodiment of a fabrication method in accordance with the present invention.

FIG. 1 shows a representative manufacturing process flow including the following steps:

Step 1. Prepare a clean substrate 100 (e.g., a silicon wafer or other solid material with flat surface) by polishing the surface or otherwise ensuring its smoothness.

Step 2. Apply a removable material on top of the substrate and pattern the material to produce a relief pattern that will serve as a positive mold scaffold 110. For example, the material may be applied directly (e.g., by pointwise deposition) in the form of the desired pattern, or may be applied to the entire surface and selectively removed.

Step 3. Coat a polymer (e.g., parylene) or polymer-containing layer 120 on top of the positive mold scaffold 110 and cure the polymer or allow it to harden. The thickness of the polymer layer 120 can be equal to or greater than 5 µm and less than or equal to 25 µm. In some embodiments, a composite layer rather than a simple polymer is employed; for example, a succession of layers (e.g., parylene-metal-parylene, with a metal such as platinum) may be sequentially coated onto the scaffold. The total thickness of the polymer-containing layer can be equal to or greater than 4 µm and less than or equal to 30 µm. Each polymer layer of the composite layer can have a thickness equal to or greater than 2 µm and less than or equal to 15 µm. The metal layer of the composite layer can have a thickness equal to or greater than 0.05 µm and less than or equal to 0.5 µm. The polymer-containing layer may further comprise one or more sets of parylene-metal layers. The parylene layer interfaces with (i.e., presents a surface to) the drug reservoir. Either the parylene layer or metal layer may interface with the electrolysis reservoir. In embodiments where the metal layer interfaces with the electrolysis reservoir, the metal (i.e. platinum) may act as a recombination catalyst and reverse the electrolysis gas production reaction. The rate of recombination may be altered by controlling the amount of recombination catalyst exposed on the membrane surface facing the electrolysis reservoir.

Step 4. Pattern the polymer layer by oxygen plasma etching using a shadow mask. The outer profile of each diaphragm is created and may include one or more tabs used for handling the diaphragm during subsequent processing steps. These tabs are later removed by mechanical or laser cutting to create the diaphragm profile to be integrated into the final product (i.e., drug pump). Additionally, this step separates one or more diaphragms from adjacent diaphragms created on a single silicon wafer.

Step 5. Soak the coated substrate in a solvent for the removable material and release the finished polymeric membrane 130.

Any suitable application method may be used in step 2, for example, pointwise deposition (e.g., using ink-jet equipment), photopatterning (e.g., photolithography), screen printing, stenciling, lamination, surface-wide coating (e.g., spin coating, wire-wound-rod coating, etc.) followed by selective removal (e.g., using a laser or a blade). Multiple coatings may be needed to achieve sufficient thickness, e.g., 100 μm.

In step 3, curing, if necessary, may be achieved in any fashion appropriate to the applied polymer, e.g., exposure to actinic radiation or simple drying. Some polymers, such as parylene, have no curing cycle.

Similarly, in step 5, the solvent is chosen based on the applied material. For example, in the case of photoresist, the solvent may be isopropyl alcohol, photoresist developer, etc. Common photoresist compositions include Hoechst AZ 4620, Hoechst AZ 4562, Shipley 1400-17, Shipley 1400-27, Shipley 1400-37, and Shipley Microposit Developer.

Figure 2:
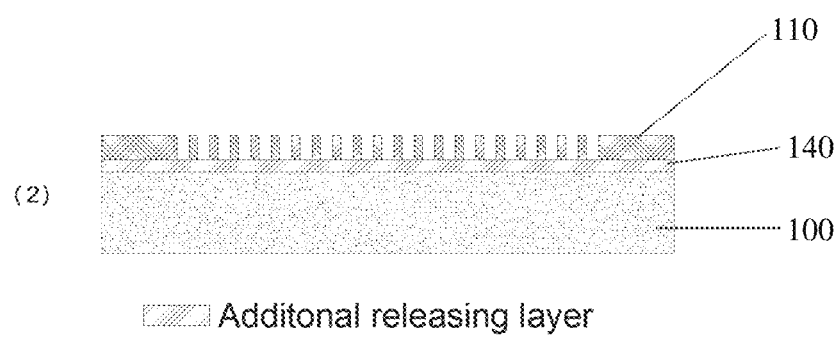
FIG. 2 illustrates the use of an additional release layer in the method shown in FIG. 1.

As illustrated in FIG. 2, an additional release layer 140 may be deposited onto the substrate 100 in order to shorten the soaking and releasing time in step 5. This release layer 140 may be the same material as the removable material 110 or a different material. For example, in the case of a photoresist layer 110, the additional layer 140 may be the same or different type of photoresist, and the layer 140 may be hard baked (i.e., baked at higher temperature or longer time) to prevent penetration by the layer 110.

Alternatively, the layer 140 may be part of the removable layer 110 deposited in accordance with step 2 as described above. In this case, the additional release layer 140 can be formed in either of two ways. One way is simply to apply separate layers of the same material sequentially, the first layer constituting the additional release layer 140 and the second receiving the mold relief pattern. Another way is to use a single layer 110 and pattern it in a manner that affects only the upper portion of the layer thickness to create the pattern. For example, if the layer 110 is a photoresist, it may be patterned using positive photolithography, which involves patternwise exposure to actinic (e.g., UV) radiation followed by subjection to a chemical developer that removes the exposed regions of the photoresist. (In negative photolithography, the unexposed regions are removed.) In this case, exposure occurs at a fluence level that affects only the top portion of the layer thickness while leaving essentially intact a bottom portion that will constitute the additional release layer; the same effect can be achieved by exposing at a higher fluence but shortening the development time. For example, if 100 μm of mold height is necessary to create the corrugations, the photoresist layer can be applied to a thickness of 120 μm, leaving 20 μm on the bottom of the corrugation structure to serve as the second release layer.

In another alternative, the additional release layer is a material different from the photoresist. For example, the additional release layer may be $SiO_2$ or a metal (e.g., aluminum, chromium, copper, gold, etc.). A $SiO_2$ layer may be applied using thermal oxidation or a chemical vapor deposition process. A metal layer can be deposited by sputtering, thermal evaporation, or e-beam evaporation. The metal may also be applied to the substrate in sheet form, e.g., using an adhesive such as epoxy.

If the additional release layer 140 is a material different from the overlying layer 110, it may require a different solvent to remove. For example, if the additional release layer 140 is $SiO_2$, hydrofluoric acid (HF) may be used first to remove the $SiO_2$ layer 140 followed by a chemical developer to remove, for example, a photoresist layer 110. If the layer is metal—e.g., aluminum—a suitable etchant is used to etch away the aluminum layer. Polymers such as parylene are not affected by these solvents and etchants.

Following removal of the additional release layer 140, the overlying structure is lifted off the substrate 100 and subjected to the action of a chemical developer to remove the layer 110. This will occur quickly due to the exposed lower surface.

Certain embodiments of the present invention have been described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of manufacturing a corrugated diaphragm suitable for use in a pump, the method comprising the steps of:
    applying a chemically removable layer onto a flat substrate, the removable layer having a relief pattern forming a positive mold therein;
    coating a membrane-forming layer comprising a hardenable polymer onto the positive mold in a liquid phase; and
    following hardening of the hardenable polymer, removing the removable layer to release the membrane-forming layer, thereby forming the corrugated diaphragm with corrugations corresponding to the relief pattern.

2. The method of claim 1, wherein the chemically removable layer is applied as a uniform coating onto the substrate and further comprising the step of patterning the uniformly applied coating to obtain the relief pattern.

3. The method of claim 2, wherein the removable layer is a photoresist and the patterning comprises (a) patternwise exposing the photoresist to actinic radiation and (b) subjecting the exposed photoresist to a developer.

4. The method of claim 3, wherein the photoresist is a positive photoresist.

5. The method of claim 3, wherein the photoresist is a negative photoresist.

6. The method of claim 1, wherein the polymer is parylene.

7. The method of claim 1, further comprising the step of patterning the membrane-forming layer by oxygen plasma etching using a shadow mask following hardening of the membrane-forming layer.

8. The method of claim 1, wherein the membrane-forming layer consists of a plurality of layers including at least one hardenable polymer layer and at least one metal layer.

9. The method of claim 1, wherein the substrate is silicon.

10. The method of claim 1, wherein the removing step comprises subjecting the removable layer to a solvent therefor.

11. The method of claim 1, further comprising applying an additional release layer onto the substrate prior to applying the membrane-forming layer.

12. The method of claim 11, wherein the additional release layer consists of a material different from the chemically removable layer.

13. The method of claim 12, wherein the releasing step comprises subjecting the additional release layer to a solvent therefor and subjecting the removable layer to a solvent therefor.

14. The method of claim 11, wherein the additional release layer consists of the same material as the chemically removable layer.

15. The method of claim 1, wherein the chemically removable layer is applied patternwise by deposition.

16. The method of claim 1, wherein the relief pattern comprises concentric circles.

17. The method of claim 1, wherein the relief pattern comprises concentric ovals.

* * * * *